(12) United States Patent
Chen et al.

(10) Patent No.: US 11,828,723 B2
(45) Date of Patent: Nov. 28, 2023

(54) METHOD FOR DETECTING AN OKADAIC ACID BASED ON A NEAR-INFRARED PHOTOELECTRIC COMPOSITE MATERIAL

(71) Applicants: JiMei University, Xiamen (CN); Xiamen Center for Disease Control and Prevention, Xiamen (CN)

(72) Inventors: Xiaomei Chen, Xiamen (CN); Chenyan Zheng, Xiamen (CN); Mingming Yin, Xiamen (CN); Bingyuan Su, Xiamen (CN); Jie Wei, Xiamen (CN)

(73) Assignees: JiMei University, Xiamen (CN); Xiamen Center for Disease Control and Prevention, Xiamen (CN)

( * ) Notice: Subject to any disclaimer, the term of this patent is extended or adjusted under 35 U.S.C. 154(b) by 230 days.

(21) Appl. No.: 17/507,340

(22) Filed: Oct. 21, 2021

(65) Prior Publication Data
US 2022/0187243 A1 Jun. 16, 2022

(30) Foreign Application Priority Data
Dec. 16, 2020 (CN) .......................... 202011488935.0

(51) Int. Cl.
*G01N 27/49* (2006.01)
*C01G 41/02* (2006.01)
(Continued)

(52) U.S. Cl.
CPC ............. *G01N 27/49* (2013.01); *C01G 41/02* (2013.01); *G01N 27/308* (2013.01);
(Continued)

(58) Field of Classification Search
CPC .. G01N 27/49; G01N 27/308; G01N 33/5438; G01N 33/5308; G01N 21/359;
(Continued)

(56) References Cited

FOREIGN PATENT DOCUMENTS

| CN | 105241931 B | 7/2016 |
|----|-------------|--------|
| CN | 108845015 B | 9/2020 |

OTHER PUBLICATIONS

Peng et al., Electrochemical synthesis of phosphorus and sulfur co-doped graphene quantum dots as efficient electrochemiluminescent immunomarkers for monitoring okadaic acid, Sensors and Actuators B: Chemical, 2020, 304, 127383, Available online Nov. 7, 2019 (Year: 2019).*

(Continued)

*Primary Examiner* — Luan V Van
*Assistant Examiner* — Shizhi Qian
(74) *Attorney, Agent, or Firm* — CALFEE HALTER & GRISWOLD LLP

(57) ABSTRACT

The present application proposes a method for detecting an okadaic acid based on a near-infrared photoelectric composite material, which includes the following steps: synthesizing $NaYF_4$: Yb, Tm up-conversion nanoparticles (UCNPs) and a semiconductor material flower-like tungsten oxide ($WO_3$) by a simple high-temperature solvothermal method; coupling the UCNPs with an okadaic acid monoclonal antibody through a classic amidation reaction to construct a competitive near-infrared photoelectrochemical immunosorbent assay (cNIR-PECIA) for okadaic acid detection. In addition, the present application employs a screen-printed carbon electrode (SPE) as the working electrode, and thus only requires a small amount of electrolytes, which is low-cost and maintenance-free.

10 Claims, 4 Drawing Sheets

(51) Int. Cl.
 *G01N 27/30* (2006.01)
 *G01N 33/543* (2006.01)
(52) U.S. Cl.
 CPC ...... *G01N 33/5438* (2013.01); *C01P 2004/03* (2013.01); *C01P 2004/32* (2013.01); *C01P 2004/61* (2013.01); *C01P 2006/40* (2013.01)
(58) Field of Classification Search
 CPC ..... G01N 21/27; C01G 41/02; C01P 2004/03; C01P 2004/32; C01P 2004/61; C01P 2006/40; C01F 17/36
 See application file for complete search history.

(56) References Cited

OTHER PUBLICATIONS

Wu et al., Simultaneous detection of microcysin-LR and okadaic acid using a dual fluorescence resonance energy transfer aptasensor, Anal Bioanal Chem, 2015, 407, 1303-1312 (Year: 2015).*

Wang et al., Synthesis of polyethylenimine/NaYF4 nanoparticles with upconversion fluorescence, Nanotechnology, 2006, 17, 5786-5791 (Year: 2006).*

Hayat et al., An electrochemical immunosensor based on covalent immobilization of okadaic acid onto screen printed carbon electrode via diazotization-coupling reaction, Talanta, 2011, 85, 513-518 (Year: 2011).*

Feng et al., A competitive-type photoelectrochemical immunosensor for aflatoxin B1 detection based on flow-like WO-3 as matrix and Ag2S-enhanced BiVO4 for signal amplification, Sensors and Actuators B: Chemical, 2018, 270, 104-111 (Year: 2018).*

Eskandani et al., Cyto/genotoxicity study of Polyoxyethylene (20) Sorbitan Monolaurate (Tween 20), DNA and Cell Biology, 2013, 32 (9) 498-503. (Year: 2013).*

* cited by examiner

METHOD FOR DETECTING AN OKADAIC ACID BASED ON A NEAR-INFRARED PHOTOELECTRIC COMPOSITE MATERIAL

CROSS REFERENCE TO RELATED APPLICATIONS

This application claims the priority of the Chinese patent application CN2020114889350, filed on Dec. 16, 2020. The contents of this Chinese patent application are all hereby incorporated by reference.

FIELD

The present application belongs to the field of toxin detection, and specifically to a method for detecting an okadaic acid based on a near-infrared photoelectric composite material.

BACKGROUND

Our country is a major producer and consumer of seafood, and the quality and safety of seafood are related to the national economy and people's livelihood. Okadaic acid (OA) is the main component of the diarrhetic shellfish poison (DSP), and its long-term toxic effect poses a serious threat to the development of shellfish aquaculture and public health. OA can induce protein hyperphosphorylation and expression of proliferation genes, leading to tumor formation. The European Food Safety Agency (EFSA) proposes in 2018 to reduce the maximum limit of OA in shellfish from 160 µg/kg to 45 µg/kg. OA is highly toxic and it is difficult to find an effective antidote therefor. Therefore, it is particularly important to develop fast, accurate and sensitive OA detection methods.

At present, for OA detection, a diversity of techniques have been established, including mouse biological, high-performance liquid chromatography-mass spectrometry, and immunosensor methods. Although the mouse biological method is simple in technology and does not require use of dedicated instruments, it is prone to large deviations and low sensitivity due to different conditions of individual mice. Although the high-performance liquid chromatography-mass spectrometry method has powerful analysis functions, it employs expensive instruments and involves a long analysis cycle, which is high in analysis cost and professional in operation, bringing a lot of inconvenience to the analysis of OA. In comparison, immunosensors, based on antibody-antigen specific binding, are simple and fast operations and low cost. Especially with the rapid development of biotechnology, some toxin antibodies with high specificity have emerged one after another, which effectively reduces the cross-reaction of antibodies and promotes the development of OA immunosensors to a certain extent. Nevertheless, in practical applications, immunosensors still have some limitations: firstly, a fixed matrix does not have a high effective loading of a toxin antibody, which directly affects the sensitivity of an immunosensor; secondly, enzymes, as the most commonly used antibody markers, involve the problems such as complex operation, being prone to inactivation, etc., which affects the stability of the sensing signal and are not conducive to improving the reproducibility of detection. In summary, discovering new sensing materials, designing and constructing an efficient immunosensing interface are important ways to achieve rapid and sensitive detection of OA.

In recent years, the working direction of most PEC sensors has been focused on using high-energy ultraviolet or visible (UV-Vis) light as an excitation light source. However, the UV-Vis light has limited penetration ability in deep tissues of a living organism and is destructive to a biomolecular structure, which is limited to analysis and detection on the surface of a living organism. In contrast, near-infrared (NIR) light with low phototoxicity and good biocompatibility is a better choice. It can avoid self-irradiation of biological tissues, thereby providing possibility of further development in in-vivo application researches. To date, there have been few reports of NIR PEC sensors because of the lack of stable NIR PEC materials. As far as we know, photosensitive materials with NIR response can be roughly classified into two categories: (1) metal sulfides with a small band gap; (2) metal oxides with stable optical absorption. The former have poor stability, while the latter typically exhibit a large band gap and limited optical absorption in UV-Vis regions. Therefore, exploring new NIR-responsive materials remains a major challenge in the construction of NIR PEC biosensors. Up-conversion luminescence (UCL) is different from general materials. It is composed of a matrix material and a luminescent center (activator and sensitizer). The energy for emitting photons is greater than but not less than the energy for excitation photons. It is a typical anti-Stokes process, in which the NIR light is usually converted into the UV-Vis light. Among many sensitizers and activators, $Yb^{3+}$ and $Er^{3+}/Tm^{3+}/Ho^{3+}$ is a classic combination, wherein $NaYF_4$: Yb, Tm up-conversion nanoparticles can emit blue light (450 nm and 480 nm) and red light (650 nm) under NIR (980 nm) excitation, and the emission spectrum thereof exactly matches the absorption spectrum of the semiconductor material tungsten oxide ($WO_3$). $WO_3$ has unique optical and electrical properties, and has been widely used in the fields such as photocatalysis, electrocatalysis, biosensing, etc.

SUMMARY

The present application aims at providing a method for detecting an okadaic acid based on a near-infrared photoelectric composite material, which synthesizes $NaYF_4$: Yb, Tm up-conversion nanoparticles and a semiconductor material tungsten oxide ($WO_3$) by a simple high-temperature solvothermal method. They form a composite material of $WO_3/NaYF_4$: Yb, Tm through reaction, which has good near-infrared photoelectric properties, and is applied to the detection of an okada acid (OA).

The present application provides a method for detecting an okadaic acid based on a near-infrared photoelectric composite material, comprising the following steps:

Step S1: mixing an okadaic acid monoclonal antibody (Anti-OA-Mab) and a phosphate buffer saline at a mass ratio of 1:1000-3000 to obtain a solution A;

Step S2: dispersing polyethyleneimine/$NaYF_4$: Yb, Tm (BPEI/UCNPs) in a phosphate buffer saline containing 1-(3-dimethylaminopropyl)-3-ethylcarbodiimide hydrochloride and N-hydroxy succinimide to obtain a solution B;

Step S3: mixing and reacting the solution A and the solution B to obtain a solution C, and dispersing a precipitate after centrifugation of the solution C in a phosphate buffer saline containing bovine serum albumin to obtain a target product $NaYF_4$: Yb, Tm-Ab (UCNPs-Ab);

Step S4: dissolving flower-like tungsten oxide (Flower-like-$WO_3$) and chitosan (CS) in ultrapure water to obtain a flower-like tungsten oxide/chitosan (Flower-like-$WO_3$/CS) suspension D;

Step S5: dropping the flower-like tungsten oxide/chitosan (Flower-like-WO$_3$/CS) suspension D on a screen-printed carbon electrode (SPE) to obtain a target product of a flower-like tungsten oxide/chitosan/screen-printed carbon electrode (Flower-like-WO$_3$/CS/SPE);

Step S6: adding an okadaic acid (OA) into a 2-morpholinoethanesulfonic acid biological buffer to obtain a solution E, and immersing the flower-like tungsten oxide/chitosan/screen-printed carbon electrode (Flower-like-WO$_3$/CS/SPE) obtained in step S5 into the solution E for reaction;

Step S7: reacting the flower-like tungsten oxide/chitosan/screen-printed carbon electrode (Flower-like-WO$_3$/CS/SPE) obtained in step S6 in an acetamide solution and a bovine serum albumin (BSA) solution containing Tween-20, respectively, to obtain a target product of an okadaic acid/flower-like tungsten oxide/chitosan/screen-printed carbon electrode (OA/Flower-like-WO$_3$/CS/SPE);

Step S8: casting a diluted solution of NaYF$_4$: Yb, Tm-Ab (UCNPs-Ab) and an okadaic acid standard solution (OA) on the okadaic acid/flower-like tungsten oxide/chitosan/screen-printed carbon electrode (OA/Flower-like-WO$_3$/CS/SPE) for reaction, and performing rinsing with a phosphate buffer saline containing Tween-20 after reaction; and Step S9: setting a bias voltage to 0 V using a chronoamperometry to test a photoelectric behavior of the okadaic acid/flower-like tungsten oxide/chitosan/screen-printed carbon electrode (OA/Flower-like-WO$_3$/CS/SPE) obtained in step S8.

In a preferred embodiment, the phosphate buffer saline has a substance concentration of 10 mmol/L and a pH of 7.4.

In a preferred embodiment, in step S2, 200 μL, 8 mg/mL of the polyethyleneimine/NaYF$_4$: Yb, Tm (BPEI/UCNPs) is dispersed in 600 μL of the phosphate buffer saline containing 10 mg/mL of the 1-(3-dimethylaminopropyl)-3-ethylcarbodiimide hydrochloride (EDC) and 5 mg/mL of the N-hydroxy succinimide (NHS).

In a preferred embodiment, in step S3, the solution A and the solution B are reacted at a temperature of 4° C. for 2 hours, the phosphate buffer saline containing 0.1% of the bovine serum albumin (BSA).

In a preferred embodiment, the ultrapure water in step S4 contains 0.3%-0.5% of the flower-like tungsten oxide (Flower-like-WO$_3$) and 0.25 wt % of the chitosan (CS).

In a preferred embodiment, the flower-like tungsten oxide/chitosan (Flower-like-WO$_3$/CS) suspension D in step S5 has a volume of 10 μL, and the flower-like tungsten oxide/chitosan/screen-printed carbon electrode (Flower-like-WO$_3$/CS/SPE) is dried at 60° C.

In a preferred embodiment, in step S6, 500 μL, 0.5 mg/mL of the okadaic acid (OA) is reacted with the 2-morpholinoethanesulfonic acid biological buffer containing 10 mg/mL of the 1-(3-dimethylaminopropyl)-3-ethylcarbodiimide hydrochloride (EDC) and 5 mg/mL of the N-hydroxysuccinimide (NHS) for 1 hour to obtain the solution E, the flower-like tungsten oxide/chitosan/screen-printed carbon electrode is reacted with the solution E for 1 hour, and the 2-morpholinoethanesulfonic acid biological buffer has a pH of 5.0 and a substance concentration of 0.1 mol/L.

In a preferred embodiment, the bovine serum albumin (BSA) solution in step S7 contains 0.05% of the Tween-20, and the bovine serum albumin (BSA) solution has a volume of 50 μL and a mass fraction of 10%.

In a preferred embodiment, in step S8, the NaYF$_4$: Yb, Tm-Ab (UCNPs-Ab) in the diluted solution of NaYF$_4$: Yb, Tm-Ab (UCNPs-Ab) and the phosphate buffer saline are mixed at a mass ratio of 1:5-20, and the phosphate buffer saline contains 0.05% of the Tween-20, okadaic acid is dispersed in 10 mmol/L phosphate buffer saline to form okadaic acid standard solution (OA) with a concentration of 0.001 to 60 ng/mL.

In a preferred embodiment, in step S8, the diluted solution of NaYF$_4$: Yb, Tm-Ab (UCNPs-Ab) and the okadaic acid standard solution (OA) are reacted with the okadaic acid/flower-like tungsten oxide/chitosan/screen-printed carbon electrode (OA/Flower-like-WO$_3$/CS/SPE) at 37° C. for 1 hour.

The present application provides a method for detecting an okadaic acid based on a near-infrared photoelectric composite material, which synthesizes NaYF$_4$: Yb, Tm up-conversion nanoparticles and a semiconductor material tungsten oxide (WO$_3$) by a simple high-temperature solvothermal method. With this method, a composite material of WO$_3$/NaYF$_4$: Yb, Tm can be obtained in a convenient, fast and controllable manner, which has good near-infrared photoelectric properties and is applied to the detection of an okadaic acid (OA). At present, there is no report on preparation of the composite material and application thereof in the field of optoelectronics. Compared with other near-infrared photoelectric materials, the present application has advantages of having simple synthesis steps, being less time-consuming and having good photoelectric properties, which is beneficial to the development of a new type of PEC biosensing platform. Compared with other OA detection methods, the present application has simple operations, high sensitivity and good stability. In addition, the present application employs an SPE (Screen-Printed Carbon Electrode) as the working electrode, and thus only requires a small amount of electrolytes, which is low-cost and maintenance-free.

BRIEF DESCRIPTION OF THE DRAWINGS

The drawings are included to provide a further understanding of the embodiments, and the drawings are incorporated into this specification and constitute a part of this specification. The drawings illustrate the embodiments and together with the description serve to explain the principles of the present application. It will be easy to recognize other embodiments and many expected advantages of the embodiments because they become better understood by referring to the following detailed description. The elements in the drawings are not necessarily in proportion to each other. The same reference numerals refer to corresponding similar components.

DETAILED DESCRIPTION

In order to make the objectives, technical solutions and advantages of the present application clearer, the present application will be further described in detail below in conjunction with the accompanying drawings. Obviously, the described embodiments are only a part of the embodiments of the present application, rather than all of them. Based on the embodiments of the present application, all other embodiments obtained by a person having an ordinary skill in the art without spending inventive efforts shall fall within the protection scope of the present application.

Figure 1:
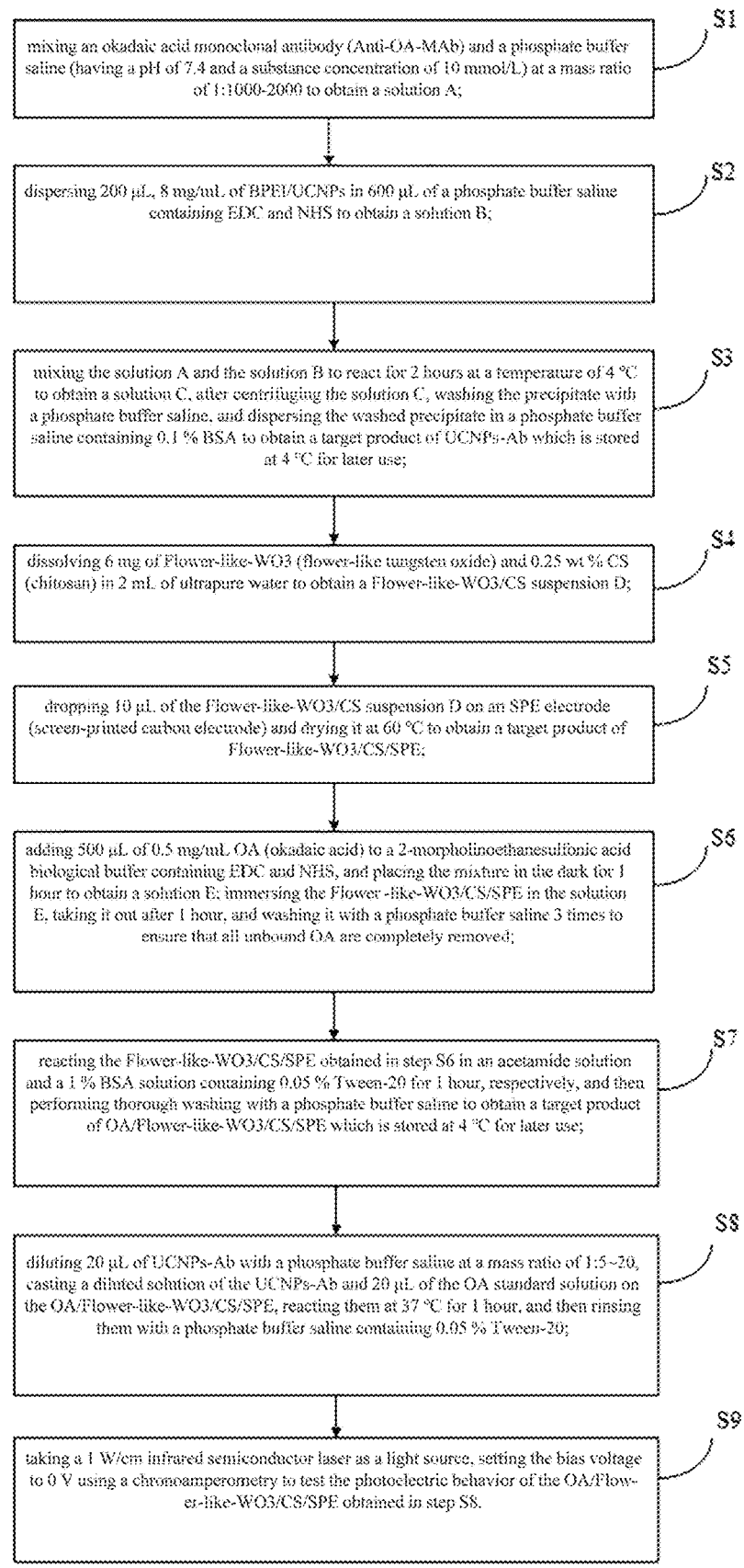
FIG. 1 is a flowchart of a method for detecting an Okadaic acid based on a near-infrared photoelectric composite material according to an embodiment of the present application.

The present application will be described in detail below with reference to FIG. 1. A method for detecting an okadaic acid based on a near-infrared photoelectric composite material according to the present application comprises the following steps:

Step S1: mixing an okadaic acid monoclonal antibody (Anti-OA-MAb) and a phosphate buffer saline (having a pH of 7.4 and a substance concentration of 10 mmol/L) at a mass ratio of 1:1000-2000 to obtain a solution A;

Step S2: dispersing 200 μL, 8 mg/mL of BPEI/UCNPs in 600 μL of a phosphate buffer saline containing EDC and NHS to obtain a solution B;

Step S3: mixing the solution A and the solution B to react for 2 hours at a temperature of 4° C. to obtain a solution C, after centrifuging the solution C, washing the precipitate with a phosphate buffer saline, and dispersing the washed precipitate in a phosphate buffer saline containing 0.1% BSA to obtain a target product of UCNPs-Ab which is stored at 4° C. for later use;

Step S4: dissolving 6 mg of Flower-like-$WO_3$ (flower-like tungsten oxide) and 0.25 wt % CS (chitosan) in 2 mL of ultrapure water to obtain a Flower-like-$WO_3$/CS suspension D;

Step S5: dropping 10 μL of the Flower-like-$WO_3$/CS suspension D on an SPE electrode (screen-printed carbon electrode) and drying it at 60° C. to obtain a target product of Flower-like-$WO_3$/CS/SPE;

Step S6: adding 500 μL of 0.5 mg/mL OA (okadaic acid) to a 2-morpholinoethanesulfonic acid biological buffer containing EDC and NHS, and placing the mixture in the dark for 1 hour to obtain a solution E; immersing the Flower-like-$WO_3$/CS/SPE in the solution E, taking it out after 1 hour, and washing it with a phosphate buffer saline 3 times to ensure that all unbound OA are completely removed;

Step S7: reacting the Flower-like-$WO_3$/CS/SPE obtained in step S6 in an acetamide solution and a 1% BSA solution containing 0.05% Tween-20 for 1 hour, respectively, and then performing thorough washing with a phosphate buffer saline to obtain a target product of OA/Flower-like-$WO_3$/CS/SPE which is stored at 4° C. for later use;

Step S8: diluting 20 μL of UCNPs-Ab with a phosphate buffer saline at a mass ratio of 1:5~20, casting a diluted solution of the UCNPs-Ab and 20 μL of the OA standard solution on the OA/Flower-like-$WO_3$/CS/SPE, reacting them at 37° C. for 1 hour, and then rinsing them with a phosphate buffer saline containing 0.05% Tween-20;

Step S9: taking a 1 W/cm infrared semiconductor laser as a light source, setting the bias voltage to 0 V using a chronoamperometry to test the photoelectric behavior of the OA/Flower-like-$WO_3$/CS/SPE obtained in step S8.

Embodiment 1: Preparation of Flower-Like-$WO_3$ (Flower-Like Tungsten Oxide)

Step S1: mixing 0.1 g of choline chloride and 16 mL of absolute ethanol to dissolve with stirring to obtain a solution A;

Step S2: adding 0.3 g of tungsten chloride to the solution A to obtain a clear solution, and continuing stirring for 10 minutes to obtain a solution B;

Step S3: adding 0.4 g of hydroquinone to the solution B to obtain a yellow turbid solution, and continuing stirring for 15 minutes to obtain a solution C;

Step S4: transferring the solution C to a 30 mL reactor, which was hydrothermally reacted at 110° C. for 4 hours;

Step S5: after the reaction is finished and cooled to room temperature, collecting the black precipitate by centrifugation, after washing with ethanol and drying, placing it in a muffle furnace for annealing at 450° C. for 30 minutes to obtain the target product of Flower-like-$WO_3$.

Figure 2:
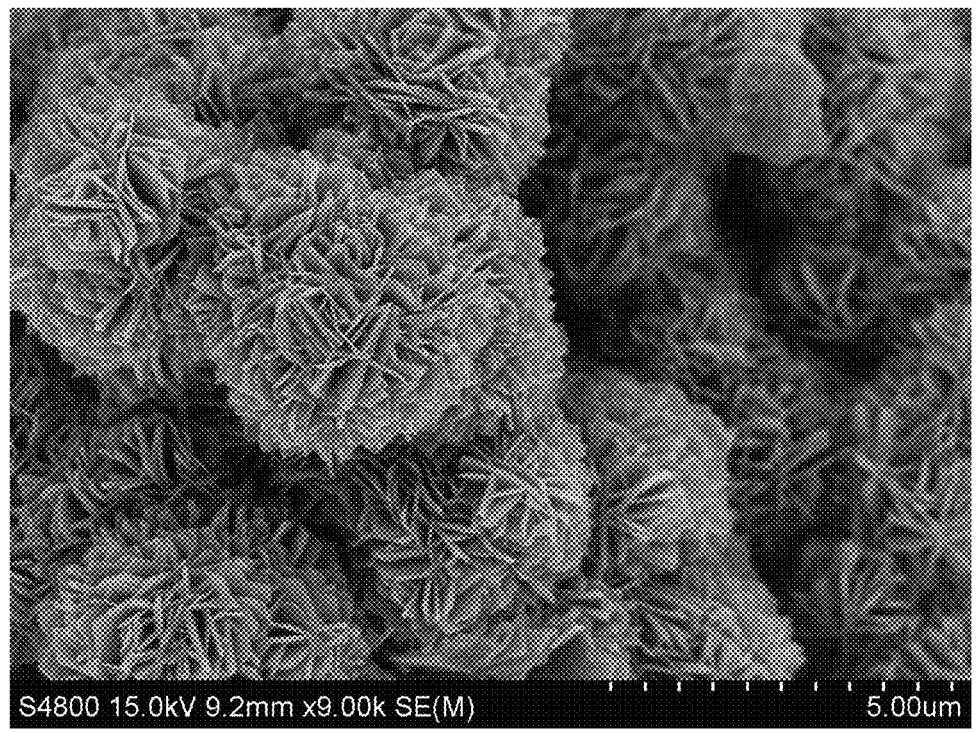
FIG. 2 is an SEM image of Flower-like-WO$_3$ according to an embodiment of the present application.

FIG. 2 is an SEM image of Flower-like-$WO_3$. As shown in FIG. 2, it can be seen that the $WO_3$ microspheres are composed of smooth nanosheets in a regular flower shape, with a single size of about 3.8 μm. The nanoflower structure can provide a larger specific surface area, which is conducive to converting light energy into electrical energy.

Embodiment 2: Preparation of BPEI/UCNP

Step S1: mixing 0.71 g of yttrium chloride, 0.23 g of ytterbium chloride, 0.02 g of thulium chloride and 30 mL of ultrapure water to dissolve with stirring to obtain a solution A;

Step S2: mixing 0.50 g of sodium fluoride and 30 mL of ultrapure water to dissolve with stirring to obtain a solution B;

Step S3: mixing 0.87 g of ethylene diamine tetraacetic acid and 50 mL of ultrapure water, which were stirred under heating to obtain a solution C;

Step S4: adding the solution A dropwise to the solution C, at which time the color of the mixed solution changes from transparent to milky white, and continuing stirring for 30 minutes to obtain a solution D;

Step S5: adding 0.1 g of polyethyleneimine to the solution D, during which the mixed solution changes from milky white to transparent again, and continuing stirring for 30 minutes to obtain a solution E;

Step S6: adding the solution C dropwise to the solution E, at which time the mixed solution becomes viscous, continuing stirring for 30 minutes to obtain a solution F;

Step S7: transfer the solution F to a 30 mL reactor, which was hydrothermally reacted in an oven at 200° C. for 2 hours;

Step S8: after the reaction is finished and cooled to room temperature, collecting the white precipitate by centrifugation, and then re-dispersing it in ultrapure water to obtain the target product of BPEI/$NaYF_4$: Yb, Tm (BPEI/UCNPs) up-conversion nanoparticles, which was stored at 4° C. in a refrigerator.

Figure 3:
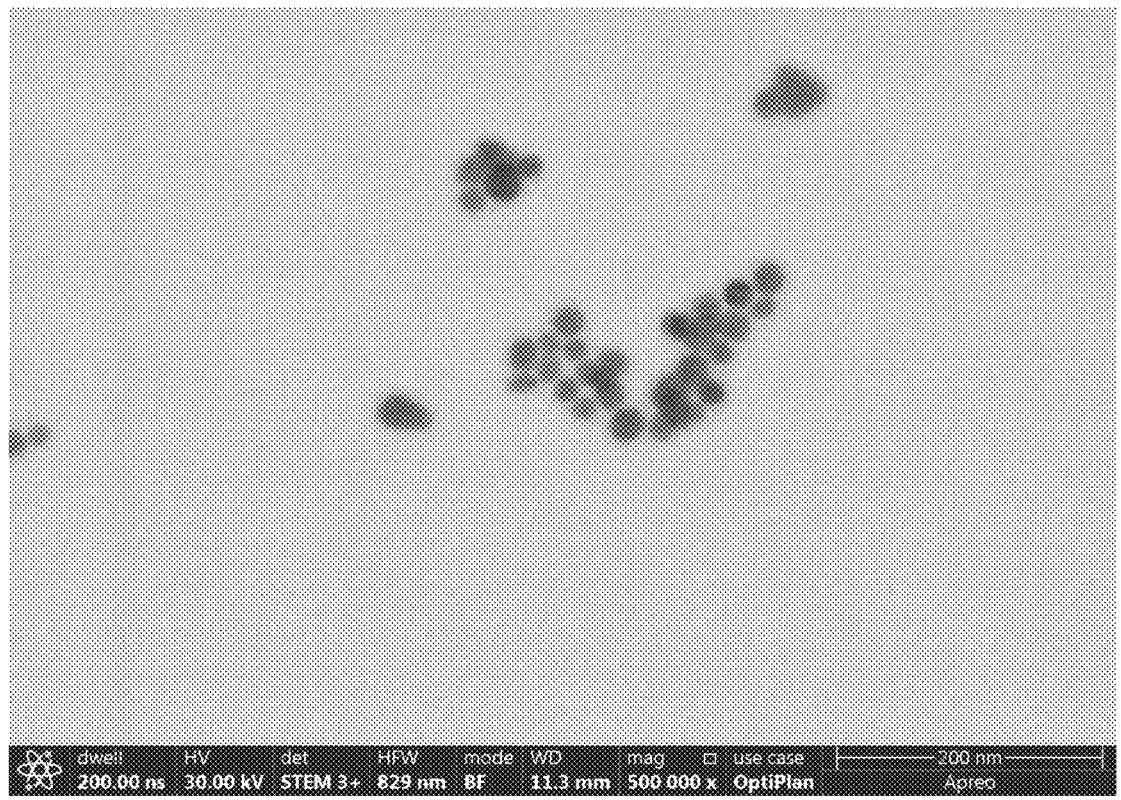
FIG. 3 is a STEM image of BPEI/UCNPs according to an embodiment of the present application.

FIG. 3 is an STEM image of BPEI/UCNPs, from which it can be seen that the prepared $NaYF_4$: Yb, Tm upconversion nanospheres have a diameter between 11 nm and 13 nm. There is a layer of light-colored substance around it, which may result from modification of the organic polymer BPEI.

Embodiment 3: Preparation of SPE

Step S1: screen printing a working electrode layer with carbon ink, and screen printing a counter electrode/reference electrode layer with carbon ink and Ag/AgCl ink.

Figure 4:
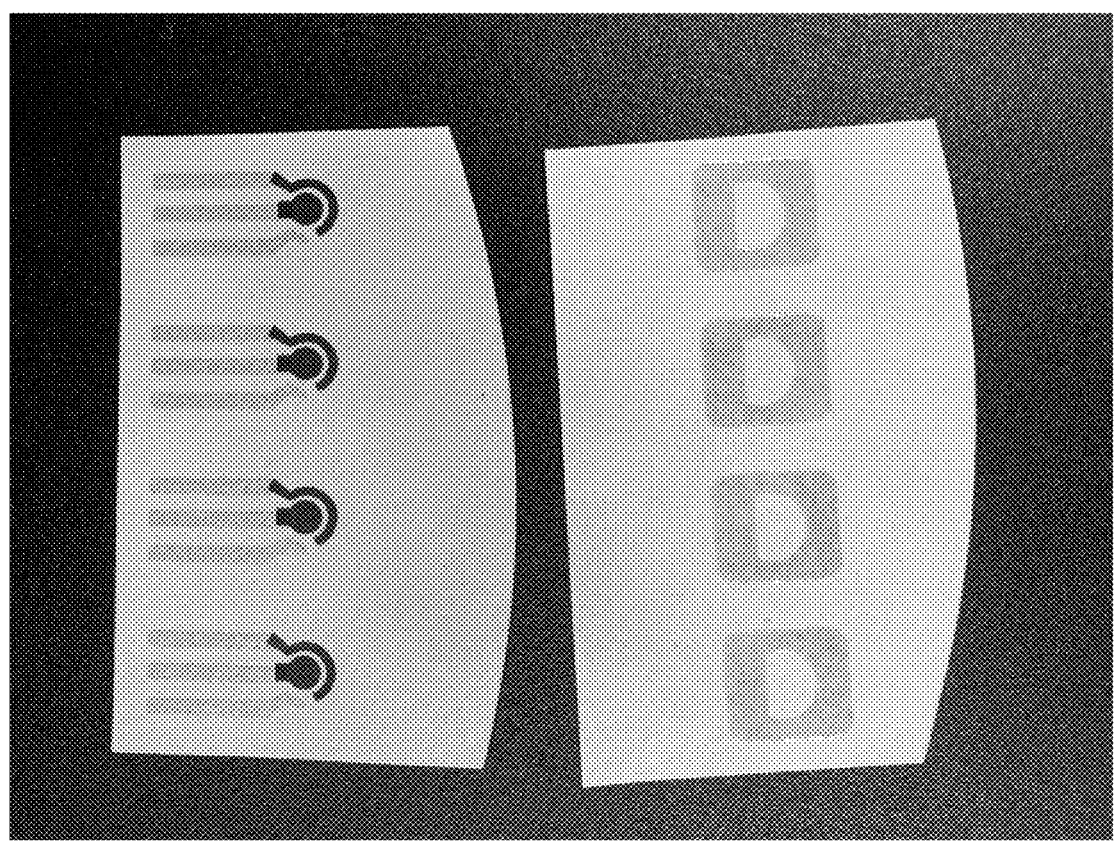
FIG. 4 is a schematic view of a real SPE according to an embodiment of the present application.

Step S2: drying each screen-printed layer at 60° C. and allowing it to cool at room temperature to obtain the target product of SPE, as shown in FIG. 4 that is a schematic view of a real SPE.

Figure 5:
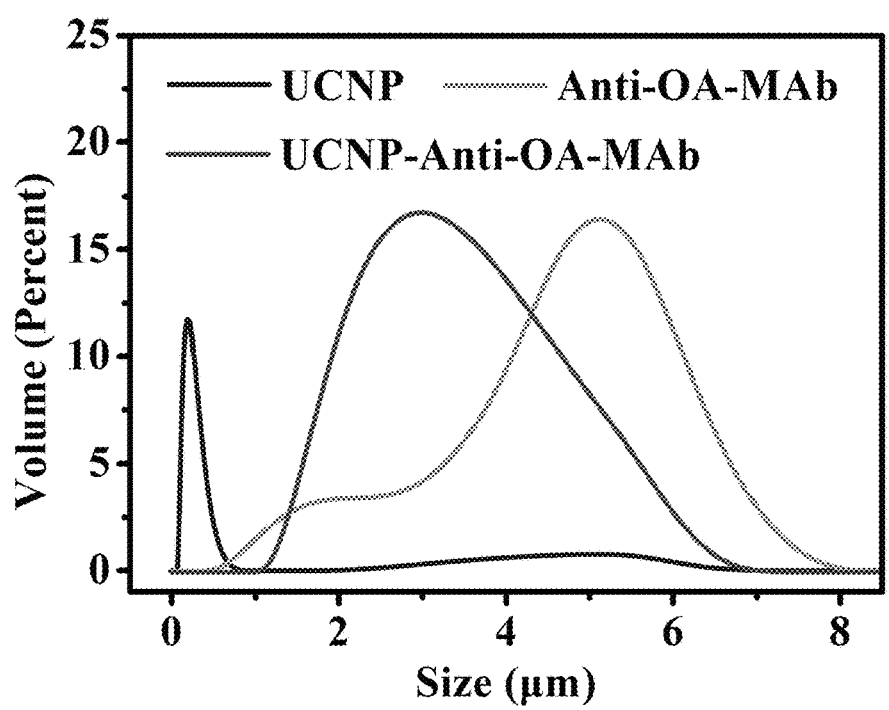
FIG. 5 is a schematic view illustrating changes in particle sizes of NaYF$_4$:Yb, Tm (UCNPs) and Anti-OA-MAb before and after coupling according to an embodiment of the present application.

FIG. 5 illustrates changes in the particle sizes of NaYF$_4$: Yb, Tm (UCNPs) and Anti-OA-MAb before and after coupling. As shown in FIG. 5, the average particle sizes of UCNPs and Anti-OA-MAb are 196.6 nm and 1545 nm respectively, and the average particle size of UCNPs-Anti-OA-MAb is 1650 nm, which is close to the sum of the particle sizes of UCNPs and Anti-OA-MAb. This proves that UCNPs can be successfully labeled on Anti-OA-MAb.

Figure 6:
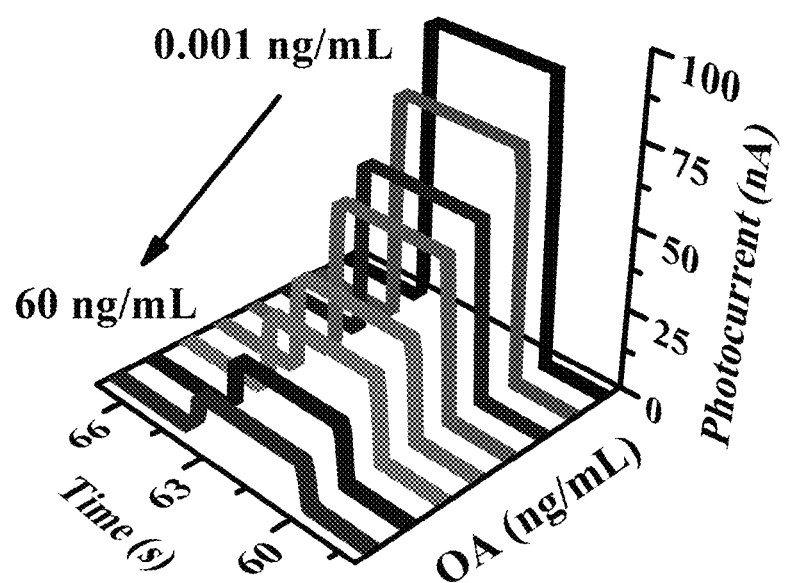
FIG. 6 is a schematic view illustrating photocurrents for detecting OAs at different concentrations according to an embodiment of the present application.

FIG. 6 is a schematic view illustrating photocurrents for detecting OAs at different concentrations. It can be clearly seen from FIG. 6 that the photocurrent signal gradually decreases as the concentration of OA increases. This is because of reduction in the number of UCNPs-Ab immunoprobes connected to the immobilized OA on the electrode, thereby resulting in a decrease in the intensity of the photocurrent. Therefore, the concentrations of free OA can be determined based on changes in the PEC intensity.

The present application provides a method for detecting an okadaic acid based on a near-infrared photoelectric composite material, which synthesizes NaYF$_4$: Yb, Tm up-conversion nanoparticles and a semiconductor material tungsten oxide (WO$_3$) by a simple high-temperature solvothermal method. With this method, a composite material of WO$_3$/NaYF$_4$: Yb, Tm can be obtained in a convenient, fast and controllable manner, which has good near-infrared photoelectric properties and is applied to the detection of an okadaic acid (OA). At present, there is no report on preparation of the composite material and application thereof in the field of optoelectronics. Compared with other near-infrared photoelectric materials, the present application has advantages of having simple synthesis steps, being less time-consuming and having good photoelectric properties, which is beneficial to the development of a new type of PEC biosensing platform. Compared with other OA detection methods, the present application has simple operations, high sensitivity and good stability. In addition, the present application employs an SPE as the working electrode, and thus only requires a small amount of electrolytes, which is low-cost and maintenance-free.

Although the principle of the present application has been described in detail above in conjunction with preferred embodiments of the present application, those skilled in the art should understand that the above-mentioned embodiments are merely explanations of exemplary implementations of the present application, and are not intended to limit the scope of the present application. The details in the embodiments do not constitute a limitation to the scope of the present application. Without departing from the spirit and scope of the present application, any obvious changes such as equivalent transformations or simple substitutions based on the technical solutions of the present application shall fall into the protection scope of the present application.

The invention claimed is:

1. A method for detecting okadaic acid based on near-infrared photoelectric composite material, wherein the following steps are comprised:
   Step S1: mixing okadaic acid monoclonal antibody and a phosphate buffer saline at a mass ratio of 1:1000-3000 to obtain a solution A;
   Step S2: dispersing polyethyleneimine/NaYF$_4$: Yb, Tm in a phosphate buffer containing 1-(3-dimethylaminopropyl)-3-ethylcarbodiimide hydrochloride and N-hydroxysuccinimide to obtain a solution B;
   Step S3: mixing and reacting the solution A and the solution B to obtain a solution C, and dispersing a precipitate after centrifugation of the solution C in a phosphate buffer containing bovine serum albumin to obtain a target product NaYF$_4$: Yb, Tm-Ab;
   Step S4: dissolving flower-shaped tungsten oxide and chitosan in ultrapure water to obtain a flower-shaped tungsten oxide/chitosan suspension D;
   Step S5: dropping the flower-shaped tungsten oxide/chitosan suspension D on a screen-printed carbon electrode to obtain a target product of a flower-shaped tungsten oxide/chitosan/screen-printed carbon electrode;
   Step S6: adding the okadaic acid into a 2-morpholinoethanesulfonic acid biological buffer to obtain a solution E, and immersing the flower-shaped tungsten oxide/chitosan/screen-printed carbon electrode obtained in step S5 into the solution E for reaction;
   Step S7: reacting the flower-shaped tungsten oxide/chitosan/screen-printed carbon electrode obtained in step S6 in an acetamide solution and a bovine serum albumin solution containing polyoxyethylene (20) sorbitan monolaurate, respectively, to obtain a target product of okadaic acid/flower-shaped tungsten oxide/chitosan/screen-printed carbon electrode;
   Step S8: casting a diluted solution of the NaYF$_4$: Yb, Tm-Ab and an okadaic acid standard solution on the okadaic acid/flower-shaped tungsten oxide/chitosan/screen-printed carbon electrode for reaction, and performing rinsing with a phosphate buffer saline containing polyoxyethylene (20) sorbitan monolaurate after reaction; and
   Step S9: setting a bias voltage to 0 V using a chronoamperometry to test a photoelectric behavior of the okadaic acid/flower-shaped tungsten oxide/chitosan/screen-printed carbon electrode obtained in step S8.

2. The method for detecting the okadaic acid based on the near-infrared photoelectric composite material according to claim 1, wherein the phosphate buffer saline has a substance concentration of 10 mmol/L and a pH of 7.4.

3. The method for detecting the okadaic acid based on the near-infrared photoelectric composite material according to claim 1, wherein in step S2, 200 μL, 8 mg/mL of the polyethyleneimine/NaYF$_4$: Yb, Tm is dispersed in 600 μL of the phosphate buffer saline containing 10 mg/mL of the 1-(3-dimethylaminopropyl)-3-ethylcarbodiimide hydrochloride and 5 mg/mL of the N-hydroxysuccinimide.

4. The method for detecting the okadaic acid based on the near-infrared photoelectric composite material according to claim 1, wherein the solution A and the solution B in step S3 are reacted at a temperature of 4° C. for 2 hours, the phosphate buffer saline containing 0.1% of the bovine serum albumin.

5. The method for detecting the okadaic acid based on the near-infrared photoelectric composite material according to claim 1, wherein the ultrapure water in step S4 contains 0.3%-0.5% of the flower-shaped tungsten oxide and 0.25 wt % of the chitosan.

6. The method for detecting the okadaic acid based on the near-infrared photoelectric composite material according to claim 1, wherein the flower-shaped tungsten oxide/chitosan suspension D in step S5 has a volume of 10 μL, and the flower-shaped tungsten oxide/chitosan/screen-printed carbon electrode is dried at 60° C.

7. The method for detecting the Okadaic acid based on the near-infrared photoelectric composite material according to claim 1, wherein 500 μL, 0.5 mg/mL of the okadaic acid in step S6 is reacted with the 2-morpholinoethanesulfonic acid biological buffer containing 10 mg/mL of the 1-(3-dimethylaminopropyl)-3-ethylcarbodiimide hydrochloride and 5 mg/mL of the N-hydroxysuccinimide for 1 hour to obtain the solution E, the flower-shaped tungsten oxide/chitosan/screen-printed carbon electrode is reacted with the solution E for 1 hour, and the 2-morpholinoethanesulfonic acid biological buffer has a pH of 5.0 and a substance concentration of 0.1 mol/L.

8. The method for detecting the okadaic acid based on the near-infrared photoelectric composite material according to claim 1, wherein the bovine serum albumin solution in step S7 contains 0.05% of the polyoxyethylene (20) sorbitan monolaurate, and the bovine serum albumin solution has a volume of 50 μL and a mass fraction of 1%.

9. The method for detecting the okadaic acid based on the near-infrared photoelectric composite material according to claim 1, wherein the $NaYF_4$: Yb, Tm-Ab in the diluted solution of the $NaYF_4$: Yb, Tm-Ab and the phosphate buffer saline in step S8 are mixed at a mass ratio of 1:5-20, the phosphate buffer saline contains 0.05% of the polyoxyethylene (20) sorbitan monolaurate, and the okadaic acid standard solution has a concentration of 0.001-60 ng/mL.

10. The method for detecting the okadaic acid based on the near-infrared photoelectric composite material according to claim 1, wherein the diluted solution of the $NaYF_4$: Yb, Tm-Ab and the okadaic acid standard solution in step S8 are reacted with the okadaic acid/flower-shaped tungsten oxide/chitosan/screen-printed carbon electrode at 37° C. for 1 hour.

\* \* \* \* \*